United States Patent [19]

Frigerio et al.

[11] Patent Number: 5,324,719
[45] Date of Patent: Jun. 28, 1994

[54] THERAPEUTICAL METHOD FOR THE TREATMENT OF HYPERTENSION

[75] Inventors: Marco Frigerio; Nicoletta Almirante, both of Milan; Alberto Cerri, Gessate MI; Tiziana Cova, Varese VA; Mara Ferrandi, Milan; Patrizia Ferrari, Varese VA, all of Italy

[73] Assignee: Sigma-Tau Industrie Farmaceutiche Riunite S.P.A., Rome, Italy

[21] Appl. No.: 79,822

[22] Filed: Jun. 22, 1993

[30] Foreign Application Priority Data

Jul. 8, 1992 [DE] Fed. Rep. of Germany ....... 4222404

[51] Int. Cl.$^5$ .............................................. A61K 31/56
[52] U.S. Cl. .................................................. 514/169
[58] Field of Search ........................................ 514/169

[56] References Cited

PUBLICATIONS

Chemical Abstracts, vol. 88, No. 13 issued 27 Mar. 1978, Gelbert et al., "Cardenolide Analogs. 7. Synthesis and Biological Activity of Some New Steriodal Guanylhydrazones," see p. 12, column 2, Abstract No. 83361j, J. Med. Chem., 21(3), 284–288.

Primary Examiner—Marianne M. Cintins
Assistant Examiner—K. Weddington
Attorney, Agent, or Firm—Oblon, Spivak, McClelland, Maier & Neustadt

[57] ABSTRACT

A therapeutical method for treating hypertension is disclosed which comprises administering to a patient in need thereof an effective amount of an imino derivative of 3$\beta$, 14$\beta$-dihydroxyetianaldehyde, particularly 17$\beta$-guanidinoiminomethyl-5$\beta$-androstan-3$\beta$,14$\beta$-diol.

2 Claims, No Drawings

THERAPEUTICAL METHOD FOR THE TREATMENT OF HYPERTENSION

The present invention relates to a therapeutical method for the treatment of hypertension in mammals, including humans.

More specifically the present invention relates to a therapeutical method which comprises administering to a hypertensive subject an effective amount of an imino derivative of 3β,14β-dihydroxyetianaldehyde having formula (I).

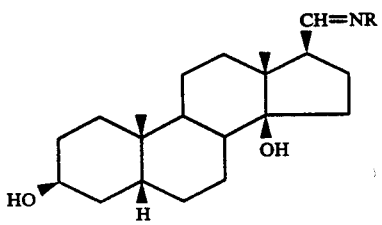

wherein
R represents $NHC(=O)NH_2$ and $NHC(=NH)NH_2$.

The two compounds of formula (I) are known compounds which were e.g. described by 1) Boutagy J., Thomas R., "Cardenolides analogues I. Route for preparing semi-synthetic analogues of digitoxigenin". Aust. J. Chem. 1971, 24, 2273;

2) Boutagy J., Gelbart A., Thomas R. "Cardenolides analogues IV. Inhibition of $Na^+$, $K^+$-ATPase". Aust. J. Pharm. Sciences 1973, 2, 41.

3β,14 β-Dihydroxyetianaldehyde is structurally related to cardiotonic steroid derivatives, known as cardenolides, such as digoxin, digitoxin and ouabain, which, as known, exhibit cardiotonic activity and are widely used in clinical practice (see for general reference: Hoffman B. F., Bigger J. T. jr. "Digitalis and allied cardiac glycosides". In the Pharmacological Basis of Therapeutics. 7th ed.; Gilmann, A. G., Goodmann, L. S., Rall, T. W., Murrad, F., Eds.; Macmillian Publishing Co.: New York, 1985; 716).

The pharmacological usefulness of cardiotonic steroids is due to their ability to increase the cardiac contractility (positive inotropic action) in patients with heart failure (Katzung B. G., Parmley W. W. "Cardiac glycosides and other drugs used in the treatment of congestive heart failure". In Basic and Clinical Pharmacology, 1987, 138). At molecular level, all therapeutically used cardiotonic steroids inhibit $Na^+$, $K^+$-ATPase, the membrane bound enzyme associated with the "sodium pump". (Repke K. R. H., Schoenfeld W., Weiland J., Megges R., Hache A. "Steroidal inhibitors of $Na^+$, $K^+$-ATPase". In Design of Enzyme Inhibitors as Drugs, Sandler M., Smith H. J. Eds.; Oxford University Press; Oxford 1989; 435).

Hoffman and Bigger (loc. cit. pp. 729-730) report that injection of ouabain in normal conscious dogs results in increasing both systolic and mean arterial pressure and that "since mean systemic arterial pressure is elevated without an increase in cardiac output, there must be an increase in systemic vascular resistance. This results from a direct effect of digitalis to cause contraction of the smooth muscle in the arterial resistance vessels. (...) Studies of effects of digitalis on the heart and circulation of normal human subjects show that, in general, the changes are similar to those described above for the dog."

Indeed studies on cardenolides have shown a significant hypertensive action of cardiac glycosides both in mammals and in humans as described for example in 1) Williams M. H., Zohman L. R., Retner A. C. "Hemodynamic effects of cardiac glycosides on normal human subjects during rest and exercise". J. Appl. Physiol. 1958, 13, 417;

2) Mason D. T., Braunwald E., Karsh R. B., Bullock F. A. "Studies on digitalis. X. Effects of ouabain on forearm vascular resistance and venous tone in normal subjects and in patients with heart failure". J. Clin. Invest. 1964, 43, 532;

3) Melville K. I., Shister H. E., Klingner B. "Comparative blood pressure and electrocardiographic changes induced by proscillaridin and ouabain". Can. J. Physiol. Pharmacol. 1966, 44, 887;

4) Reuter N., Meyer Fr. "Wirkung von Pentaformylgitoxin (Gitoformate) auf das Herz-Kreislaufsystem narkotisierter Katzen". Arzneim.-Forsch. 1976, 26, 1201).

Thomas and coworkers described a series of cardenolide analogues possessing positive inotropic activity. The compounds described by Thomas, in particular derivatives of 3β, 14β-dihydroxyetianaldehyde, were able to inhibit $Na^+$, $K^+$-ATPase in 1) Boutagy J., Thomas R., "Cardenolides analogues I. Route for preparing semi-synthetic analogues of digitoxigenin". Aust. J. Chem. 1971, 24, 2273;

2) Boutagy J., Thomas R., "Cardenolides analogues III. Synthesis of C17α- and C17β- (α,β-unsaturated) esters, ketones, nitriles and related derivatives from digitoxigenin". Aust. J. Pharm. Sciences, 1973, 2, 9;

3) Boutagy J., Gelbart A., Thomas R. "Cardenolides analogues IV. Inhibition of $Na^+$, $K^+$-ATPase". Aust. J. Pharm. Sciences 1973, 2, 41;

4) Thomas R., Boutagy J., Gelbart A. "Cardenolides analogs V. Cardiotonic activity of semisynthetic analogs of digitoxigenin". J. Pharmacol. Exp. Ther. 1974, 191, 219;

5) Gelbart A., Thomas R. "Cardenolide analogues 7. Synthesis and biological activity of some new steroidal guanylhydrazones". J. Med. Chem. 1978, 21, 284.

We have now surprisingly found that the imino derivatives of 3β,14β-dihydroxyetianaldehyde of formula (I), while inhibit $Na^+,K^+$-ATPase in vitro, show a marked antihypertensive action when tested in vivo.

The present invention also encompasses within its scope the E and Z geometric isomers, their mixtures, the tautomers and their mixtures, the metabolites and the metabolic precursors of compounds of formula (I) as well as the pharmaceutically acceptable salts thereof for preparing the above-metioned pharmaceutical compositions.

Pharmaceutically acceptable salts of (I) are salts which retain the biological activity of the base and are derived from such known pharmacologically acceptable acids such as hydrochloric, sulphuric, phosphoric, malic, tartaric, maleic, citric, methanesulphonic or benzoic acids.

Preferably the salt is the hydrochloride or the phosphate salt.

The compounds of formula (I) and their pharmaceutically acceptable salts may also form pharmaceutically acceptable solvates, such as for example hydrates, which are also encompassed within the scope of this invention.

The following examples illustrate the preparation of the compounds which are used as antihypertensive agents according to the present invention.

PREPARATION 1

17β-ureidoiminomethyl-5β-androstan-3β,14β-diol Ia

To a solution of 88.0 mg of semicarbazide hydrochloride and 65 μl of pyridine in 3 ml of water, a solution of 250 mg of 3β,14β-dihydroxyetianaldehyde in 10 ml of methanol was added slowly, at room temperature. After 4 hours, the methanol was evaporated and the resulting mixture was extracted with chloroform. The organic solution was dried over anhydrous sodium sulfate and evaporated to dryness. The crude residue was purified by flash-chromatography ($SiO_2$) using chloroform/methanol 93/7 as eluent to give 180 mg of the title compound as monohydrate. The title compound (Ia) is a white solid, mp 222°–226° C. (emihydrate mp 258°–262° C.: Boutagy J., Thomas R., Aust. J. Chem., 1971, 24, 2723).

TLC: Rf=0.35 ($SiO_2$ plates, chloroform/methanol 95/5).

$^1$H NMR (300 MHz, $CDCl_3$, ppm from TMS): 0.90 (3H, s); 0.97 (3H, s); 2.35–2.45 (1H, m); 4.13 (1H, bs); 5.3 (2H, bb); 7.22 (1H, d); 7.78 (1H, s).

PREPARATION 2

17β-Guanidinoiminomethyl-5β-androstan-3β,14β-diol Ib

To a solution of 15.0 g of $NaH_2PO_4$ and 3.20 g of aminoguanidine hydrogencarbonate in 300 ml of water and 150 ml of dioxane heated at reflux, a solution of 5.00 g of 3β,14β-dihydroxyetianaldehyde in dioxane was added during 1.5 hours. After 0.5 hour at reflux the solution was evaporated to dryness under reduced pressure. The solid was ground in water containing 30% of ethanol and 0.650 g of sodium hydroxide. After filtration and drying, the solid was first ground in diethyl ether containing 5% of ethyl acetate and then crystallized from ethyl acetate to give 3.00 g of the title compound (Ib) as a white solid, mp 163°–165° C. (dihydrate mp 159°–164° C.: Boutagy J., Thomas R., Aust. J. Pharm. Sciences, 1973, 2, 9).

TLC: Rf=0.24 ($SiO_2$ plates, chloroform/methanol/ammo-nia solution 30% 80/20/3).

$^1$H NMR (300 MHz, $DMSO-d_6$, ppm from TMS): 0.75 (3H, s); 0.87 (3H, s); 2.18–2.30 (1H, m); 3.87 (2H, s); 4.18 (1H, d); 4.95 (2H, bs); 5.40 (2H, bs); 7.40 (1H, d).

Compounds (I) and their pharmaceutically acceptable salts and solvates are useful agents for the treatment of hypertension.

The ability of the compounds of this invention to lower blood pressure was tested by using different animal models with genetic arterial hypertension, as described in the following example.

EXAMPLE

In the models of essential hypertension, the following rat strains were used:

1) Milan spontaneously Hypertensive rats Strain (MHS), (Bianchi G., Ferrari P., Barber B. "The Milan Hypertensive strain". In Handbook of Hypertension, Vol. 4; Experimental and Genetic Models of Hypertension., W. de Jong Eds., Elsevier Science Publishers 1984; 328), and 2) Spontaneously Hypertensive Rats (SHR), (Okamoto K., Aoki K. "Development of a strain of spontaneously hypertensive rats". Japan Circulation J. 1963, 27, 282).

The procedure adopted to test the antihypertensive activity of the compounds (I) on each of the above mentioned models was the following: systolic blood pressure (SBP) and heart rate (HR) were measured by an indirect tail-cuff method in three-month old hypertensive rats (either MHS or SHR) before beginning the treatment (basal values). The rats were then subdivided in two groups of at least 7 animals each, one receiving the compound and the other, the control group, receiving only the vehicle. The compound, suspended in METHOCEL ® 0.5% (w/v), was administered daily by mouth, for ten days. SBP and HR were measured daily 6 and 24 hours after the treatment. At the end of the ten day treatment period, a washout period of at least two days was carried out, in order to check how long the SBP was maintained low or the basal values were reestablished.

Experimental data for compound Ib are reported in the following tables [MHS (Table 1), SHR (Table 2)]: compound Ia shows similar, although less pronounced, antihypertensive action.

TABLE 1

SYSTOLIC BLOOD PRESSURE FALL*
IN MILAN HYPERTENSIVE RATS (MHS)

| Compd. n° | DOSE** mg/Kg/os | During treatment | | After washout | |
|---|---|---|---|---|---|
| | | SBP mm Hg | HR beats/min | SBP mm Hg | HR beats/min |
| Controls | vehicle | 170 +/−2.5 | 327 +/−7.5 | 171 +/−2.4 | 317 +/−6.3 |
| DIGI | 10 | 172 +/−2.0 | 320 +/−11.8 | 167 +/−2.5 | 312 +/−8.0 |
| Ib | 10 | 154 +/−5.3 | 334 +/−3.7 | 170 +/−1.6 | 338 +/−6.0 |

DIGI = digitoxigenin
*recorded 6 hours after oral administration.
**in METHOCEL ® 0.5% w/v

TABLE 2

SYSTOLIC BLOOD PRESSURE FALL* IN SPONTANEUOSLY HYPERTENSIVE RATS (SHR)

| Compd. n* | DOSE** mg/Kg/os | During treatment | | After washout | |
|---|---|---|---|---|---|
| | | SBP mm Hg | HR beats/min | SBP mm Hg | HR beats/min |
| Controls | vehicle | 196 +/−4.5 | 402 +/−9.5 | 194 +/−3.0 | 413 +/−8.3 |
| DIGI | 10 | 193 +/−3.5 | 410 +/−11.2 | 190 +/−4.5 | 400 +/−10.0 |
| Ib | 10 | 157 +/−5.0 | 395 +/−4.9 | 187 +/−3.0 | 402 +/−7.0 |

DIGI = digitoxigenin
*recorded 6 hours after oral admninistration.
**in METHOCEL ® 0.5% w/v The administration of compound of formula (I) or pharmaceutically acceptable salts as well as acceptable solvates thereof, may be by oral or parenteral route.

The pharmaceutical composition for use in accordance with the present invention may be formulated in conventional manner using one or more physiologically acceptable carriers or excipients.

Thus the compounds of formula (I) and their pharmacologically acceptable salts and solvates may be formulated for oral, parenteral or rectal administration.

The amount required to treat hypertension depends on the relative efficacies of the compounds of invention, the nature and the severity of the disorders being treated, the weight of the mammal and the route of administration.

Examples of pharmaceutical composition suited to the oral administration comprise capsules, soft capsules, tablets, granulates, powders, solutions, lyophilized vials, sachets, possible sustained-release forms, containing from 0.05 to 300 mg of the active ingredient per unit dose which could be administered 1 to 4 times per day accordingly to the diagnosis and to the patients conditions.

For parenteral administrations, both intravenous and intramuscular, suitable forms are lyophilized vials or sterile solutions containing 0.01-200 mg of the active ingredients to be administered 1 to 3 times per day.

Compounds (I) are administered preferably by oral route, being the pharmaceutical composition tablets or capsules, prepared by conventional means with pharmaceutically acceptable excipients such as binding agents (e.g. maize starch, polyvinylpyrrolidone or hydroxypropylmethylcellulose), fillers (e.g. lactose, microcrystalline cellulose or calcium hydrogenphosphate), lubricants (e.g. magnesium stearate, talc or silica), disintegrants (e.g. potato starch or sodium starch glycollate) or wetting agents (e.g. sodium lauryl sulfate).

What is claimed is:

1. A therapeutical method for the treatment of hypertension which comprises administering to a hypertensive subject an effective amount of an imino derivative of 3β,14β-dihydroxy-etianaldehyde having formula (I)

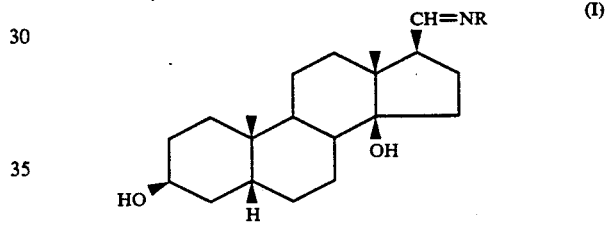

wherein R is NHC(=O)NH$_2$ and NHC(=NH)NH$_2$ or a pharmaceutically acceptable salt, solvate, geometric isomer, tautomer or mixtures thereof.

2. The method of claim 1, wherein said imino derivative is 17β-guanidinoiminomethyl-5β-androstan-3β,14β-diol.

* * * * *